United States Patent [19]
Hibi et al.

[11] Patent Number: 5,118,895
[45] Date of Patent: Jun. 2, 1992

[54] PROCESS FOR PREPARING ALKYL-SUBSTITUTED AROMATIC HYDROCARBON

[75] Inventors: Takuo Hibi, Toyonaka; Masami Fukao, Kurita; Kiyoshi Ikimi, Oita; Gohfu Suzukamo, Ibaraki, all of Japan

[73] Assignee: Sumitomo Chemical Co., Ltd., Osaka, Japan

[21] Appl. No.: 668,787

[22] Filed: Mar. 13, 1991

[30] Foreign Application Priority Data

Mar. 14, 1990 [JP] Japan ................ 2-64728

[51] Int. Cl.$^5$ ................ C07C 2/64
[52] U.S. Cl. ................ 585/452; 585/467; 585/468
[58] Field of Search ........ 585/452, 467, 468, 453

[56] References Cited

U.S. PATENT DOCUMENTS

| | | | |
|---|---|---|---|
| 2,769,850 | 11/1956 | Closson et al. | 585/452 |
| 2,771,495 | 11/1956 | Pines et al. | 585/452 |
| 2,780,660 | 2/1957 | Field et al. | 585/452 |
| 3,244,758 | 4/1966 | Eberhardt | 585/452 |
| 4,511,748 | 4/1985 | Kudoh et al. | 585/467 |
| 4,720,601 | 1/1988 | Suzukamo et al. | 585/377 |
| 4,922,054 | 5/1990 | Smith | 585/452 |
| 4,929,783 | 5/1990 | Smith | 585/452 |
| 4,977,124 | 12/1990 | Smith | 502/174 |

FOREIGN PATENT DOCUMENTS

| | | |
|---|---|---|
| 0328940 | 2/1989 | European Pat. Off. |
| 61-110332 | 3/1986 | Japan |
| 1-242885 | 8/1989 | Japan |
| 2-068625 | 3/1990 | Japan |
| 2-068801 | 3/1990 | Japan |
| 1259535 | 8/1969 | United Kingdom |
| 1269280 | 8/1969 | United Kingdom |

OTHER PUBLICATIONS

"Carbanions Additions in the Reaction of Aromatic Hydrocarbons with Monoolefins" by Herman Pines and Victor Mark, vol. 78.

Primary Examiner—Asok Pal
Attorney, Agent, or Firm—Birch, Stewart, Kolasch & Birch

[57] ABSTRACT

An alkyl-substituted hydrocarbon is prepared effectively under mild conditions by alkylating an alkyl aromatic hydrocarbon having at least one hydrogen atom at an alpha-position in a side chain with an olefin in the presence of a solid base which is obtainable by treating a water-containing oxide of an alkaline earth metal with at least one material selected from the group consisting of alkali metals and alkali metal hydrides in an amount of 0.5 to 3.5 equivalents per one mole of water in said oxide in an inert gas atmosphere.

13 Claims, No Drawings

PROCESS FOR PREPARING ALKYL-SUBSTITUTED AROMATIC HYDROCARBON

BACKGROUND OF THE INVENTION

1. Field of the Invention

The present invention relates to a process for preparing an alkyl-substituted aromatic hydrocarbon. More particularly, the present invention relates to a process for preparing an alkyl-substituted aromatic hydrocarbon by reacting an alkyl aromatic hydrocarbon having at least one hydrogen atom at an alpha-position in said alkyl side chain with an olefin in the presence of a solid base which is obtainable by heating a water-containing oxide of an alkaline earth metal and at least one material selected from the group consisting of alkali metals and alkali metal hydrides, whereby the hydrogen atom at the alpha-position is substituted with an alkyl group.

2. Description of the Related Art

The alkyl-substituted aromatic hydrocarbons are useful as intermediates in the production of fine chemicals such as agricultural chemicals, pharmaceuticals and other chemicals and prepared by reacting the aromatic hydrocarbon having the hydrogen atom at the alpha-position in the side chain with the olefin in the presence of a base catalyst.

As the preparation process of the alkyl-substituted aromatic hydrocarbon, there are known a process which utilizes a catalyst comprising metal sodium and chlorotoluene and a process which utilizes a catalyst comprising metal sodium supported on potassium carbonate (cf. J. Am. Chem. Soc., 78, 4316 (1956), GB Patent No. 1269280 and Japanese Patent Kokai Publication No. 53229/1986).

However, the conventionally used catalysts have various drawbacks such as insufficient catalytic activities, a low yield of the alkyl-substituted hydrocarbon per a unit amount of the catalyst and troublesome separation of the catalysts from the product.

SUMMARY OF THE INVENTION

One object of the present invention is to provide a base catalyst which effectively catalyzes a reaction of an aromatic hydrocarbon having a hydrogen atom at the alpha-position in a side chain with an olefin and which can be easily separated from the product after the reaction.

Another object of the present invention is to provide a process for preparing an alkyl-substituted hydrocarbon by reacting the alkyl aromatic hydrocarbon having the hydrogen atom at the alpha-position in the side chain with the olefin.

Accordingly, the present invention provides a process for preparing an alkyl-substituted hydrocarbon comprising alkylating an alkyl aromatic hydrocarbon having at least one hydrogen atom at an alpha-position in a side chain with an olefin in the presence of a solid base which is obtainable by heating and reacting a water-containing oxide of an alkaline earth metal and at least one material selected from the group consisting of alkali metals and alkali metal hydrides in an amount of 0.5 to 3.5 equivalents per one mole of water in said oxide in an inert gas atmosphere.

DETAILED DESCRIPTION OF THE INVENTION

The process of the present invention is characterized in the use of the specific solid base as the catalyst, which solid base is prepared from the water-containing oxide of the alkaline earth metal. The alkaline earth metal oxide includes oxides of the elements of Group II of the Periodic Table. Preferably, oxides of magnesium and calcium are used. More preferably, magnesium oxide is used. Two or more alkaline earth metal oxides may be used as a mixture.

The water-containing oxide of the alkaline earth metal is prepared by calcining hydroxide and oxide of the alkaline earth metal. According to the calcining temperature and time, the water content varies so that various oxide which has desired content of water can be produced.

The water content may be expressed by weight loss on heating the oxide up to 800° C. The water content is usually from 1 to 10% by weight based on the weight of the oxide.

As the alkali metal or its hydride, an alkali metal of Group I of the Periodic Table such as lithium, sodium, potassium and rubidium or its hydride is used. They may be used as a mixture. Among them, sodium, potassium, sodium hydride, potassium hydride, or mixture of them, particularly potassium and its hydride are preferred. The amount of the alkali metal or its hydride is generally from 0.5 to 3.5 equivalents, preferably from 0.9 to 2.5 equivalents per one mole of water contained in the alkaline earth metal oxide.

Examples of the inert gas are nitrogen, helium, argon, and the like.

In the preparation of the solid base, the watercontaining alkaline earth metal oxide and the alkali metal or its hydride are heated in the inert gas atmosphere. A heating temperature is usually from 150° to 600° C., preferably from 180° to 400° C.

A heating time varies with other reaction conditions such as the reaction temperature. It is usually from 10 to 300 minutes.

By the above heating, the solid base which has high catalytic activity and handleability can be obtained.

In the process of the present invention, the aromatic hydrocarbon having the hydrogen atom at the alpha-position in the side chain is reacted with the olefin in the presence of the above described solid base as the catalyst.

As such aromatic hydrocarbon, not only monocyclic aromatic hydrocarbon but also condensed polycyclic aromatic hydrocarbon may be used. In the aromatic hydrocarbons, the side chains may be closed to form a ring. Specific examples of the aromatic hydrocarbon are toluene, ethylbenzene, isopropylbenzene (cumene), n-propylbenzene, n-butylbenzene, sec.-butylbenzene, isobutylbenzene, xylene, cymene, diisopropylbenzene, methylnaphthalene, tetrahydronaphthalene, indan and the like. Among them, toluene, ethylbenzene and isopropylbenzene are preferred.

As the olefin, those having 2 to 20 carbon atoms are usually used. The olefin may be straight or branched. The carbon-carbon double bond may be a terminal or internal double bond. Preferably, the olefin having the terminal double bond is used. Specific examples of the olefin are ethylene, propylene, 1-butene, 2-butene, isobutylene, 1-pentene, 2-pentene, 1-hexene, 2-hexene, 3-hexene, 1-heptene, 2-heptene, 3-heptene, octene, nonene, 3-methyl-1-butene, 2-methyl-2-butene, 3-methyl-1-pentene, 3-methyl-2-pentene and the like. Among them, ethylene, propylene, 1-butene and 2-butene are preferred.

The alkylation reaction according to the present invention may be carried out batchwise or continuously with the use of a fluidized bed or a fixed bed.

The reaction temperature for the alkylation is usually from 0° to 300° C., preferably from 20° to 200° C.

The reaction pressure is from atmospheric pressure to 200 kg/cm$^2$, preferably from 2 to 100 kg/cm$^2$.

The molar ratio of the olefin to the aromatic hydrocarbon is usually from 0.1 to 10, preferably from 0.2 to 5.

In the batchwise reaction, the amount of solid base catalyst to be used is from 0.01 to 20% by weight, preferably from 0.05 to 5% by weight based on the weight of the aromatic hydrocarbon. The reaction time is generally from 0.5 to 50 hours, preferably from 1 to 25 hours.

In the continuous reaction, the mixture of the aromatic hydrocarbon and the olefin in the above molar ratio is supplied at LHSV of 0.1 to 1000 hr$^{-1}$, preferably 0.5 to 500 hr$^{-1}$.

According to the present invention, the alkyl-substituted hydrocarbon is effectively prepared in the presence of the solid base catalyst in a small amount under the mild conditions. Further, the catalyst to be used according to the present invention is easily handled and post-treated after the reaction.

PREFERRED EMBODIMENTS OF THE INVENTION

Practically and presently preferred embodiments of the present invention will be illustrated by following examples.

The water content in the alkaline earth metal oxide is measured by weighing an oxide sample filled in a quartz glass tube in a nitrogen atmosphere, heating the sample in a tubular furnace to 800° C. with flowing nitrogen in the quartz glass tube, keeping it at the same temperature for 2 hours, cooling it to room temperature, weighing the sample weight and then calculating the water content from the weight loss of the sample.

Preparation of Solid Bases

Solid Base A

Magnesium oxide containing 2.8% by weight of water (a calcined product of Starmag U manufactured by Konoshima Chemical Industry Co., Ltd.) (20 g) was charged in a 500 ml flask under nitrogen. Then, to the flask containing magnesium oxide, metal potassium (1.96 g) was added at 290° C. under nitrogen while stirring and a resulting mixture was stirred at the same temperature for 0.2 hours, followed by cooling to room temperature to obtain Solid Base A (21.7 g).

Solid Base B

In the same manner as in the preparation of Solid Base A but using 1.62 g of metal potassium, Solid Base B was prepared.

Solid Base C

In the same manner as in the preparation of Solid Base A but using 2.6 g of metal potassium, Solid Base C was prepared.

Solid Base D

In the same manner as in the preparation of Solid Base A but using 1.2 g of metal potassium, Solid Base D was prepared.

Solid Base E

In the same manner as in the preparation of Solid Base A but using 1.2 g of metal potassium and adding potassium at 200° C. Solid Base E was prepared.

Solid Base F

In the same manner as in the preparation of Solid Base A but using 2.1 g of metal sodium in place of metal potassium, Solid Base F was prepared.

Solid Base G

To calcium oxide containing 1.8% by weight of water (a calcined product of First Grade calcium hydroxide) (20 g), metal potassium (0.47 g) was added at 290° C. under nitrogen while stirring and a resulting mixture was stirred at the same temperature for 0.2 hours, followed by cooling to room temperature to obtain Solid Base G.

Solid Base H

To the same magnesium oxide as used in the preparation of Solid Base A (20 g), potassium hydride (1.91 g) was added at 360° C. under nitrogen while stirring and a resulting mixture was stirred at the same temperature for 0.2 hours, followed by cooling to room temperature to obtain Solid Base H.

Solid Base I

In the same manner as in the preparation of Solid Base H but using 1.87 g of sodium hydride in place of potassium hydride, Solid Base I was prepared.

Solid Base J

To the same calcium oxide as used in the preparation of Solid Base G (20 g), potassium hydride (0.88 g) was added at 360° C. while stirring and a resulting mixture was stirred at the same temperature for 0.2 hours, followed by cooling to room temperature to obtain Solid Base J.

Solid Base K

In the same manner as in the preparation of Solid Base A but using anhydrous magnesium oxide, Solid Base K was prepared.

Solid Base L

To magnesium oxide containing 10.9% by weight of water (20 g), metal potassium (1.96 g) was added at 290° C. under nitrogen while stirring and a resulting mixture was stirred at the same temperature for 0.2 hours, followed by cooling to room temperature to obtain Solid Base L.

Solid Base M

In the same manner as in the preparation of Solid Base A but using 1.94 g of potassium hydride in place of metal potassium, Solid Base M was prepared.

Example 1

In a 600 ml autoclave equipped with a magnetic stirrer, Solid Base A (0.15 g) and cumene (240 g) were charged under nitrogen, heated to 160° C. while stirring at 1000 rpm and then reacted at the same temperature for 0.5 hours while supplying ethylene gas under pressure of 10 kg/cm$^2$G to prepare tert.-amylbenzene (hereinafter referred to as "TAB").

After the reaction, the autoclave was cooled, and the catalyst was filtered off. The reaction mixture was analyzed by gas chromatography. The results are shown in Table 1.

Examples 2-10 and Comparative Examples 1 and 2

In the same manner as in Example 1 but using each of Solid Bases A to L and carrying the reaction under the conditions shown in Table 1, the alkylation was carried out. The results are shown in Table 1.

In Examples 1 though 10, the catalysts were still active at the end of the reaction, and the alkylation could be further carried out by using the same catalysts.

Comparative Example 3

To a 200 ml autoclave equipped with a magnetic stirrer, anhydrous potassium carbonate which had been dried by heating under nitrogen at 400° C. for 2 hours (8.19 g), sodium (0.30 g) and cumene (26.7 g) were charged under nitrogen and heated to 190° C., followed by stirring at the same temperature for 2 hours at 1000 rpm.

Then, the autoclave was cooled, and cumene (53.3 g) was additionally supplied. The mixture was heated to 160° C. while stirring at 1000 rpm. At the same temperature, the reaction was continued for 3 hours while supplying ethylene gas under pressure of 10 kg/cm$^2$G. The results are also shown in Table 1.

The selectivity of TAB is calculated according to the following equation:

TABLE 1

$$\text{Selectivity (\%)} = \frac{\text{Amount of produced TAB (mole)} \times 100}{\text{Total amount of all produced alkyl-substituted compounds (mole)}}$$

| Example No. | Solid Base (g) | Reaction time (hrs) | Conversion of cumene (%) | Selectivity of TAB (%) |
|---|---|---|---|---|
| 1 | A(0.15) | 0.5 | 98.5 | 99.3 |
| 2 | A(0.16) | 0.5 | 98.7 | 99.4 |
| 3 | B(0.23) | 0.5 | 94.3 | 96.9 |
| 4 | C(0.16) | 0.5 | 58.8 | 99.9 |
| 5 | D(0.18) | 0.5 | 99.7 | 99.5 |
| 6 | E(0.29) | 1.0 | 32.6 | 99.9 |
| 7 | G(1.32) | 1.0 | 99.8 | 99.9 |
| 8 | H(0.16) | 2.0 | 96.5 | 99.9 |
| 9 | I(0.18) | 1.0 | 18.1 | 99.9 |
| 10 | J(0.46) | 1.0 | 38.8 | 99.9 |
| Com. 1 | K(0.46) | 0.5 | 9.8 | 61.5 |
| Com. 2 | L(1.29) | 0.5 | 0 | 0 |
| Com. 3 | Mixture (8.49) | 3 | 19.4 | 73.9 |

Example 11

In a 300 ml autoclave equipped with a magnetic stirrer, Solid Base D (3.02 g) and toluene (80 g) were charged under nitrogen and then liquid propylene (70 ml) was charged under pressure. The mixture was reacted at 160° C. for 6 hours while stirring at 1000 rpm to obtain isobutylbenzene (hereinafter referred to as "IBB").

After the reaction, the product was analyzed in the same manner as in Example 1. The results are shown in Table 2.

Example 12

In the same manner as in Example 11 but using Solid Base M and carrying out the reaction under the conditions shown in Table 2, the alkylation was carried out. The results are shown in Table 2.

In Examples 11 and 12, the catalysts were still active at the end of the reaction and the alkylation could be further carried out by using the same catalyst.

Comparative Example 4

In a 200 ml autoclave equipped with a magnetic stirrer, anhydrous potassium carbonate which had been calcined at 400° C. for 2 hours under nitrogen (8.45 g), sodium (0.30 g) and toluene (26.6 g) were charged and stirred at 1000 rpm at 190° C. for 2 hours under nitrogen. After cooling the autoclave, toluene (53.2 g) was further added and then liquid propylene (70 ml) was charged under pressure. The mixture was reacted at 160° C. for 6 hours while stirring. The results are shown in Table 2.

The selectivity of IBB is calculated according to the following equation:

TABLE 2

$$\text{Selectivity (\%)} = \frac{\text{Amount of produced IBB (mole)} \times 100}{\text{Total amount of all produced alkyl-substituted compounds (mole)}}$$

| Example No. | Solid base (g) | Conversion of toluene (%) | Selectivity of IBB (%) |
|---|---|---|---|
| 11 | D(3.02) | 30.2 | 87.2 |
| 12 | M(3.12) | 19.6 | 89.2 |
| Com. 4 | Mixture (8.75) | 3.5 | 89.2 |

What is claimed is:

1. A process for preparing an alkyl-substituted hydrocarbon comprising alkylating an alkyl aromatic hydrocarbon having at least one hydrogen atom at an alpha-position in a side chain with an olefin in the presence of a solid base which is obtainable by heating and reacting a water-containing oxide of an alkaline earth metal and at least one material selected from the group consisting of alkali metals and alkali metal hydrides in an amount of 0.5 to 3.5 equivalents per one mole of water in said oxide in an inert gas atmosphere.

2. The process according to claim 1, wherein a heating temperature is from 150° to 600° C.

3. The process according to claim 1, wherein a water content in said alkaline earth metal oxide is from 1 to 10% by weight.

4. The process according to claim 1, wherein said alkaline earth metal oxide is one selected from the group consisting of magnesium oxide and calcium oxide.

5. The process according to claim 4, wherein said alkaline earth metal oxide is magnesium oxide.

6. The process according to claim 1, wherein said material is at least one selected from the group consisting of sodium, potassium, sodium hydride and potassium hydride.

7. The process according to claim 1, wherein said material is potassium.

8. The process according to claim 1, wherein said material is potassium hydride.

9. The process according to claim 1, wherein an amount of said material is from 0.9 to 2.5 equivalents per one mole of a water content in said alkaline earth metal oxide.

10. The process according to claim 1, wherein said aromatic hydrocarbon is at least one selected from the group consisting of toluene, ethylbenzene and isopropylbenzene.

11. The process according to claim 1, wherein said olefin is at least one selected from the group consisting of ethylene, propylene, 1-butene and 2-butene.

12. The process according to claim 1, wherein an alkylation temperature is from 0° to 300° C.

13. The process according to claim 1, wherein an amount of said solid base is 0.01 to 20% by weight based on a weight of said aromatic hydrocarbon.

* * * * *